(12) United States Patent
Matsuyama et al.

(10) Patent No.: US 8,844,146 B2
(45) Date of Patent: Sep. 30, 2014

(54) EYEGLASS FRAME SHAPE MEASUREMENT DEVICE

(75) Inventors: Yoshinori Matsuyama, Anjo (JP); Yasumasa Iida, Toyokawa (JP); Takayasu Yamamoto, Toyokawa (JP)

(73) Assignee: Nidek Co., Ltd., Aichi (JP)

( * ) Notice: Subject to any disclaimer, the term of this patent is extended or adjusted under 35 U.S.C. 154(b) by 182 days.

(21) Appl. No.: 13/614,509

(22) Filed: Sep. 13, 2012

(65) Prior Publication Data

US 2013/0067754 A1    Mar. 21, 2013

(30) Foreign Application Priority Data

Sep. 21, 2011 (JP) ................................. 2011-205483
Sep. 21, 2011 (JP) ................................. 2011-206646

(51) Int. Cl.
| | | |
|---|---|---|
| A61B 3/10 | (2006.01) | |
| B43L 9/00 | (2006.01) | |
| B43L 11/00 | (2006.01) | |
| G01B 1/00 | (2006.01) | |
| G01B 3/14 | (2006.01) | |
| G01B 5/20 | (2006.01) | |
| A61B 3/11 | (2006.01) | |
| G02C 13/00 | (2006.01) | |
| B24B 9/14 | (2006.01) | |

(52) U.S. Cl.
CPC . *G01B 5/20* (2013.01); *A61B 3/111* (2013.01); *G02C 13/003* (2013.01); *B24B 9/144* (2013.01); *G02C 13/005* (2013.01)
USPC ........ 33/200; 33/28; 33/507; 33/551; 33/553; 33/554

(58) Field of Classification Search
CPC .... G02C 13/005; G02C 13/003; A61B 3/111; B24B 9/144; G01B 5/20
USPC ..................... 33/28, 200, 507, 551, 553, 554
See application file for complete search history.

(56) References Cited

U.S. PATENT DOCUMENTS

| | | | |
|---|---|---|---|
| 6,325,700 B1 | 12/2001 | Mizuno et al. | |
| 6,350,190 B1 | 2/2002 | Matsuyama | |
| 2002/0026722 A1* | 3/2002 | Suzuki et al. | 33/200 |
| 2011/0131822 A1* | 6/2011 | Matsuyama | 33/200 |
| 2011/0131823 A1 | 6/2011 | Matsuyama | |

FOREIGN PATENT DOCUMENTS

| | | |
|---|---|---|
| JP | 2000-314617 A | 11/2000 |
| JP | 2001-174252 A | 6/2001 |
| JP | 2011-122898 A | 6/2011 |
| JP | 2011-122899 A | 6/2011 |

* cited by examiner

*Primary Examiner* — Peter Macchiarolo
*Assistant Examiner* — Rhyan C Lange
(74) *Attorney, Agent, or Firm* — Sughrue Mion, PLLC

(57) ABSTRACT

An eyeglass frame shape measurement device includes: an eyeglass frame holding unit including a first slider and a second slider for holding an eyeglass frame; a rim measuring unit including a tracing stylus for a rim of the eyeglass frame, and detecting the movement position of the tracing stylus to measure a shape of the rim; a template holder configured to attach a template and a measurement object of a demo lens; a template measuring unit including a tracing stylus shaft configured to contact an edge of the measurement object attached to the template holder, for measuring radius vector information of the measurement object; and a housing portion provided to house the template holder and provided in one of the first slider and the second slider when measurement using the template measuring unit is not being performed.

9 Claims, 11 Drawing Sheets

EYEGLASS FRAME SHAPE MEASUREMENT DEVICE

CROSS-REFERENCE TO RELATED APPLICATION

This application is based upon and claims the benefit of priority of Japanese Patent Application No. 2011-205483 filed on Sep. 21, 2011 and Japanese Patent Application No. 2011-206646 filed on Sep. 21, 2011, the contents of which are incorporated herein by reference in its entirety.

BACKGROUND

The present invention is related to an eyeglass frame shape measurement device that measures the shape of a rim of an eyeglass frame, and relates to an eyeglass frame shape measurement device that can measure the shape of a template (or a demo lens).

An eyeglass frame shape measurement device is known including an eyeglass frame holding mechanism that holds an eyeglass frame in a desired state, and a measuring mechanism that moves a tracing stylus inserted into a groove of a rim (lens frame) of the eyeglass frame along the groove of the rim, and detects the movement of the tracing stylus to obtain the three-dimensional shape of the rim (for example, refer to JP-A-2000-314617 and JP-A-2011-122899).

The eyeglass frame holding mechanism includes a first slider and a second slider for pressing the right and left rims of the eyeglass frame from a longitudinal direction (longitudinal direction when wearing the eyeglass frame) and determining the longitudinal positions of the right and left rims. A clamp mechanism having clamp pins for clamping the left rim and the right rim, respectively, is provided inside each slider. The rims of the eyeglass frame are clamped by the clamp pins and the interval between the first slider and the second slider is narrowed, whereby the right and left rims of the eyeglass frame are held in a predetermined state. In this state, the tracing stylus is inserted into the groove of one rim, and the three-dimensional shape of the rim is measured.

Additionally, in this type of measurement device, a template (including a demo lens attached to a rim of the eyeglass frame) can be measured. In the template measurement, a template holder that is a jig for attaching the template is used, the template holder is attached to an attachment portion provided separately from the eyeglass frame holding mechanism, and the template is set at a predetermined measurement position with respect to the measuring mechanism. Since the template holder is unnecessary during measurement of the eyeglass frame and becomes obstructive, the template holder is detached from the attachment portion.

Additionally, in recent years, a high curve frame in which the warpage of a rim is large has being increasing. In order to measure the rim of the high curve frame with high precision, an eyeglass frame shape measurement device is proposed, which traces the rim by making the tip (tracing stylus shaft) of the tracing stylus tiltable according to the height of the warpage (perpendicular direction) of the rim (for example, refer to JP-A-2001-174252 and JP-A-2011-122898).

SUMMARY

In the eyeglass frame shape measurement devices of the related art, the template holder detached from the attachment portion is kept in a place different from the measurement device or is kept in a housing portion provided in a cover (a cover of a processing device in a case where the eyeglass frame shape measurement device is integrally assembled into an eyeglass lens periphery processing device) of the measurement device. However, in a system in which the template holder is kept in the place different from the measurement device, the template holder may be missing or may not be able to be immediately taken out in use. In the configuration in which a housing place for the template holder is provided in the cover of the measurement device (or processing device), there is a problem in that the device may be enlarged or the housing place should be secured according to the cover of the measurement device or the processing device, and consideration for such a design is required.

In the measuring mechanism of the template, it is advantageous that the tracing stylus shaft for measurement of a rim be also used as a tracing stylus shaft that contacts the edge of the template. However, in JP-A-2011-122898 in which the tracing stylus shaft is made tiltable there is a configuration in which a side surface where the tilt of the tracing stylus shaft is not generated contacts the template. In order to further improve the precision of the followability of template tracing, mechanisms of the device cannot but become complicated and enlarged. Additionally, control of measurement pressure also becomes complicated. In the configuration in which the tracing stylus shaft for template measurement is exclusively provided, the device becomes complicated and costs become high.

An aspect of the present invention has been made in consideration of the devices of the related art, and a technical object thereof is to provide an eyeglass frame shape measurement device with a user-friendly template holder, even if a template holder housing place is not provided in a cover or the like of a device. Additionally, another technical object of the aspect of the invention is to provide an eyeglass frame shape measurement device that can improve the precision of template measurement without causing complication of a configuration and high costs even in template measurement while enabling a rim of a high curve frame to be measured with high precision.

In order to solve the above objects, the aspect of the present invention provides the following configurations.

(1) An eyeglass frame shape measurement device comprising:

an eyeglass frame holding unit including a first slider and a second slider which are configured to hold an eyeglass frame;

a rim measuring unit including a tracing stylus to be inserted into a groove of a rim of the eyeglass frame, the rim measuring unit being configured to detect the movement position of the tracing stylus to measure a shape of the rim;

a template holder configured to attach and a measurement object of a demo lens and a template;

a template measuring unit including a tracing stylus shaft configured to contact an edge of the measurement object attached to the template holder, the template measuring unit being configured to detect the movement of the tracing stylus shaft in a radial direction of the measurement object to measure radius vector information of the measurement object; and a housing portion provided to house the template holder and provided in one of the first slider and the second slider when measurement using the template measuring unit is not being performed.

(2) The eyeglass frame shape measurement device according to (1), wherein each of the first slider and the second slider includes a left rim clamp mechanism including a clamp pin for clamping a left rim and a right rim clamp mechanism including a clamp pin for clamping a right rim, at least one of the first slider and the second slider has a space formed between the left rim clamp mechanism and the right rim clamp mechanism, the space being formed by denting an upper portion of the slider, and the housing portion is provided in the space.

(3) The eyeglass frame shape measurement device according to (1), wherein an upper portion of a center of one of the first slider and the second slider in a lateral direction in which the first slider and the second slider extend is dented, and the housing portion is provided in the space.

(4) The eyeglass frame shape measurement device according to (1) further comprising an attachment portion to which the template holder is detachably attached.

(5) The eyeglass frame shape measurement device according to (1), wherein the template holder has a lateral dimension, a longitudinal dimension, and a height dimension so as to fall within a lateral dimension, a longitudinal dimension, and a height dimension of the housing portion.

(6) The eyeglass frame shape measurement device according to (1), wherein the rim measuring unit includes:

a tracing stylus holding unit including a tracing stylus shaft that has the tracing stylus attached to an upper portion thereof, the tracing stylus holder unit being configured to hold the tracing stylus shaft so as to be tiltable in a tip direction of the tracing stylus;

a tilt angle detecting unit configured to detect a tilt angle of the tracing stylus shaft;

a moving unit configured to two-dimensionally move the tracing stylus holding unit in the radial direction of the rim; and a rotating unit configured to rotate the tracing stylus holding unit around an axis perpendicular to the radial direction, and the rim measuring unit is used as the template measuring unit, and the tracing stylus shaft is used as the tracing stylus shaft that contacts the edge of the measurement object, the eyeglass frame shape measurement device further comprises:

a measurement mode selection unit configured to select a rim measurement mode and a template measurement mode;

a control unit configured to control the rotating unit and the moving unit so that a back surface of the tracing stylus shaft located opposite the tracing stylus contacts the edge of the measurement object in template measurement mode; and an arithmetic unit configured to obtain the radius vector information of the measurement object based on position information of the tracing stylus holding unit in the radial direction, rotation information of the rotating unit, and detection information of the tilt angle detecting unit, and during measuring the measurement object, the control unit controls the rotating unit and the moving unit so that the tilt of the tracing stylus shaft is kept perpendicular to the edge of the measurement object when the back surface of the tracing stylus shaft contacts the edge of the measurement object, based on the detected information.

(7) The eyeglass frame shape measurement device according to (6), wherein the arithmetic unit corrects the position information of the tracing stylus holding unit in the radial direction to obtain the radius vector information of the measurement object, based on the tilt angle detected by the tilt angle detecting unit.

(8) The eyeglass frame shape measurement device according to (6) further comprising:

a first measurement pressure applying mechanism configured to apply measurement pressure so that the tracing stylus shaft is tilted in the tip direction of the tracing stylus in the rim measurement mode;

a second measurement pressure applying mechanism configured to apply measurement pressure so that the back surface of the tracing stylus shaft is tilted toward the edge of the measurement object in the template measurement mode; and a switching unit configured to switch between the first measurement pressure applying mechanism and the second measurement pressure applying mechanism.

(9) The eyeglass frame shape measurement device according to (6), wherein the control unit stops the measurement operation of the template measuring unit in a case where the tilt angle detected by the tilt angle detecting unit exceeds a predetermined range.

According to the invention, user-friendliness of the template holder can be improved even if the template holder housing place is not provided in the cover or the like of the device. Additionally, the precision of the template measurement can be improved without causing complication of a configuration and high costs even in the template measurement while enabling the high curve frame to be measured with high precision.

DESCRIPTION OF EXEMPLARY EMBODIMENTS

Figure 1:
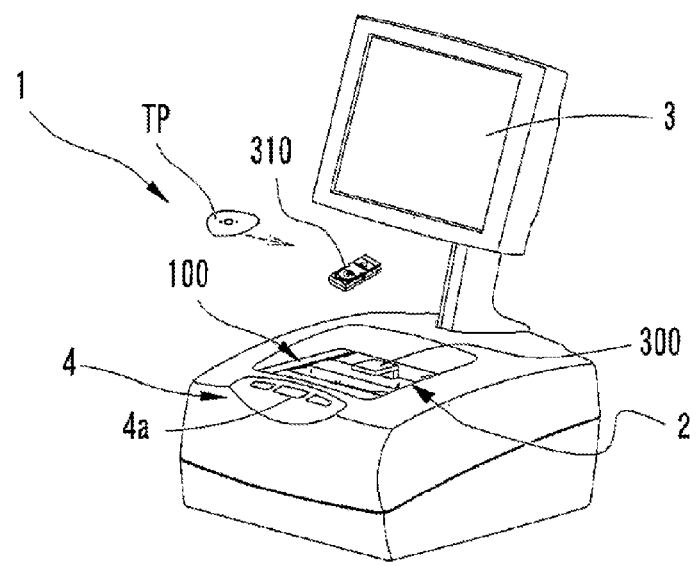
FIG. 1 is a schematic appearance view of an eyeglass frame shape measurement device.

An embodiment of the invention will be described below with reference to the drawings. FIG. 1 is a schematic appearance view of an eyeglass frame shape measurement device. An eyeglass frame shape measurement device 1 includes a frame holding unit 100 that holds an eyeglass frame F in a desired state, and a measuring unit 200 that measures the three-dimensional shape of a rim (target lens shape) by inserting a tracing stylus into a groove of the rim of the eyeglass frame held by the frame holding unit 100 and by detecting the movement of the tracing stylus. A cover of the measurement device 1 has an opening window 2, and the frame holding unit 100 is arranged below the opening window 2. Additionally, an attachment portion 300 for detachably attaching a template holder 310 to be used when measuring a measurement object TP (hereinafter abbreviated as template TP) of a template or a demo lens attached to the template or the eyeglass frame is arranged behind the center of the device 1 in a lateral direction. The measuring unit 200 that is a rim measuring unit is also used as a template measuring unit for measuring the template TP attached to the template holder 310.

A switch section 4 with a measurement starting switch or the like is arranged on the front side of a housing of the device 1. A panel section 3 with a touch panel display is arranged on the rear side of the housing of the device 1. During rim processing of an eyeglass lens, the layout data of the lens with respect to target lens shape data, the processing conditions of the lens, and the like are input by the panel section 3. The three-dimensional shape data of a rim obtained in the device 1 and the data input in the panel section 3 are transmitted to an eyeglass lens rim processing device. In addition, the device 1 may be incorporated into the eyeglass lens rim processing device, similarly to JP-A-2000-314617.

Figure 2A:
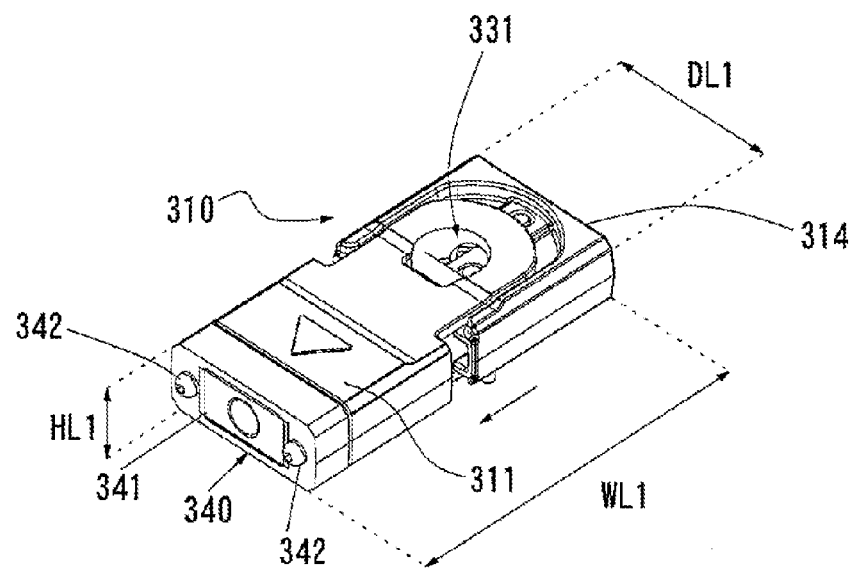
FIG. 2A is a schematic configuration view of a template holder, and is a perspective view of the front surface of the template holder.
Figure 2B:
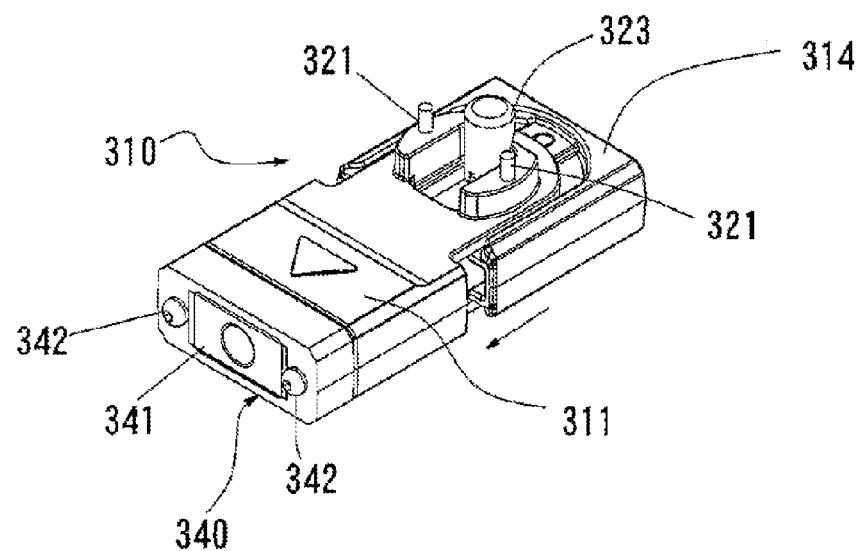
FIG. 2B is a schematic configuration view of the template holder, and is a perspective view of the back surface of the template holder.

FIG. 2 is a schematic configuration view of the template holder 310, FIG. 2A is a perspective view of the front surface of the template holder 310, and FIG. 2B is a perspective view of the back surface of the template holder 310. The template holder 310 has a body portion 311, and a mounting surface 340 for mounting the attachment portion 300 on one end of the body portion 311 in the longitudinal direction. The mounting surface 340 is provided with a magnet 341, and two pins 342 that fit holes formed on the attachment portion 300 side. As shown in FIG. 2A, the front surface side of the body portion 311 is formed with an insertion hole 331 for mounting the base of a cup CU fixed to the front surface of a demo lens. A pushing member 314 always biased to the side apart from the body portion 311 by a spring (not shown) arranged inside the body portion 311 is arranged at the other end of the body portion 311 of the longitudinal direction. The base of the cup CU is mounted into the insertion hole 331 in a state where the pushing member 314 is pushed into the body portion 311 side, and the demo lens is held by the template holder 310 as the pushing member 314 is returned to its original state.

As shown in FIG. 2B, a central pin 323 inserted into a central hole that the template TP has, and two small pins 321 inserted into two small holes that the template TP has are provided in the back surface side of the body portion 311. The central pin 323 is fixed to the pushing member 314 and is moved together with the pushing member 314. The template TP is held by the template holder 310 as the pushing member 314 is returned to its original state after the central hole of the template TP is fitted to the central pin 323 and the small hole of the template TP is fitted to the small pins 321 in a state where the pushing member 314 is pushed into the body portion 311 side.

Figure 3:
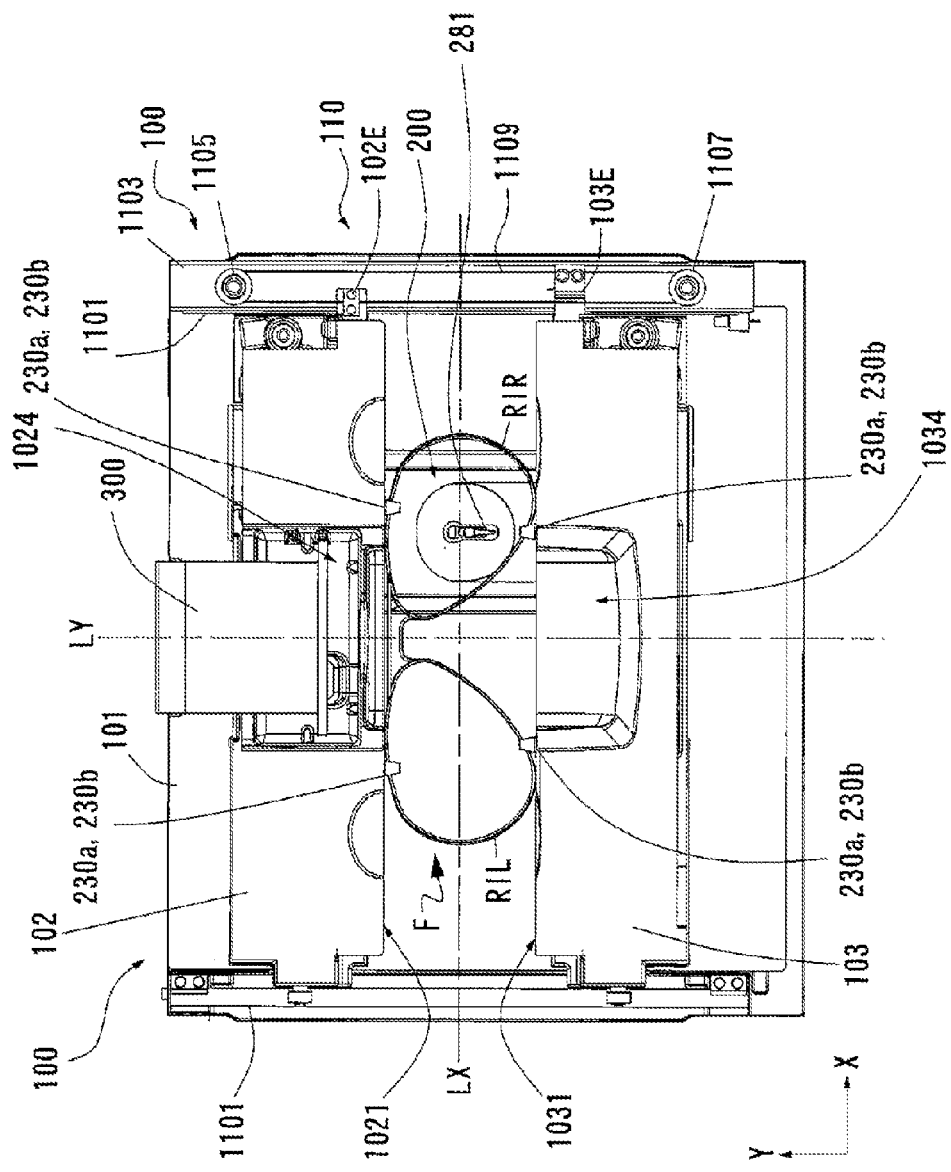
FIG. 3 is a top view of a frame holding unit in a state where an eyeglass frame is held.

FIG. 3 is a top view of the frame holding unit 100 in a state where the eyeglass frame F is held. The lateral direction in FIG. 3 is defined as an X direction, and the longitudinal direction is defined as a Y direction. The radial direction of the rim of the eyeglass frame F is defined as an XY direction. A perpendicular direction orthogonal to the XY direction is defined as the Z direction. Hereinbelow, the up-and-down direction of the device 1 is defined as the perpendicular direction (Z direction) (the longitudinal direction in a state where a user wears the eyeglass frame F).

A measuring unit 200 is provided on the bottom side of the frame holding unit 100. A first slider 102 and a second slider 103 for holding the eyeglass frame F substantially horizontally are placed on the holding section base 101. The first slider 102 has a first surface 1021 that abuts on the top sides, in the longitudinal direction, of a left rim RIL and a right rim RIR of the frame F. The second slider 103 has a second surface 1031 that abuts on the bottom sides, in the longitudinal direction, of the left rim RIL and the right rim RIR. The first surface 1021 and the second surface 1031 face each other.

The first surface 1021 of the first slider 102 and the second surface 1031 of the second slider 103 are held so as to be movable by an opening and closing moving mechanism 110 in directions in which the interval between both the sliders is opened and closed (in a direction in which the interval between both the sliders is widened and in a direction in which the interval between both the surfaces is narrowed). The opening and closing moving mechanism 110 includes two guide rails 1101 that are arranged on the right and left of a holding section base 101 and extend in the Y direction, two pulleys 1105 and 1107 that are arranged in the Y direction on the right in FIG. 3, and a wire 1109 stretched over the two pulleys 1105 and 1107, and a spring 1110 (refer to FIG. 5) that always biases the first slider 102 and the second slider 103 in a direction in which the interval between the sliders is closed. In FIG. 3, a right end portion 102E of the first slider 102 is attached to the left of the wire, and a right end portion 103E of the second slider 103 is attached to the right of the wire. The first slider 102 and the second slider 103 are held by the opening and closing moving mechanism 110 having these configurations so as to be movable in the direction in which the interval between both the sliders is widened and in the direction where the interval between both the sliders is narrowed, around a centerline LX between both the sliders. If either the first slider 102 or the second slider 103 is moved, the other one also moves in an interlocking manner.

Figure 4:
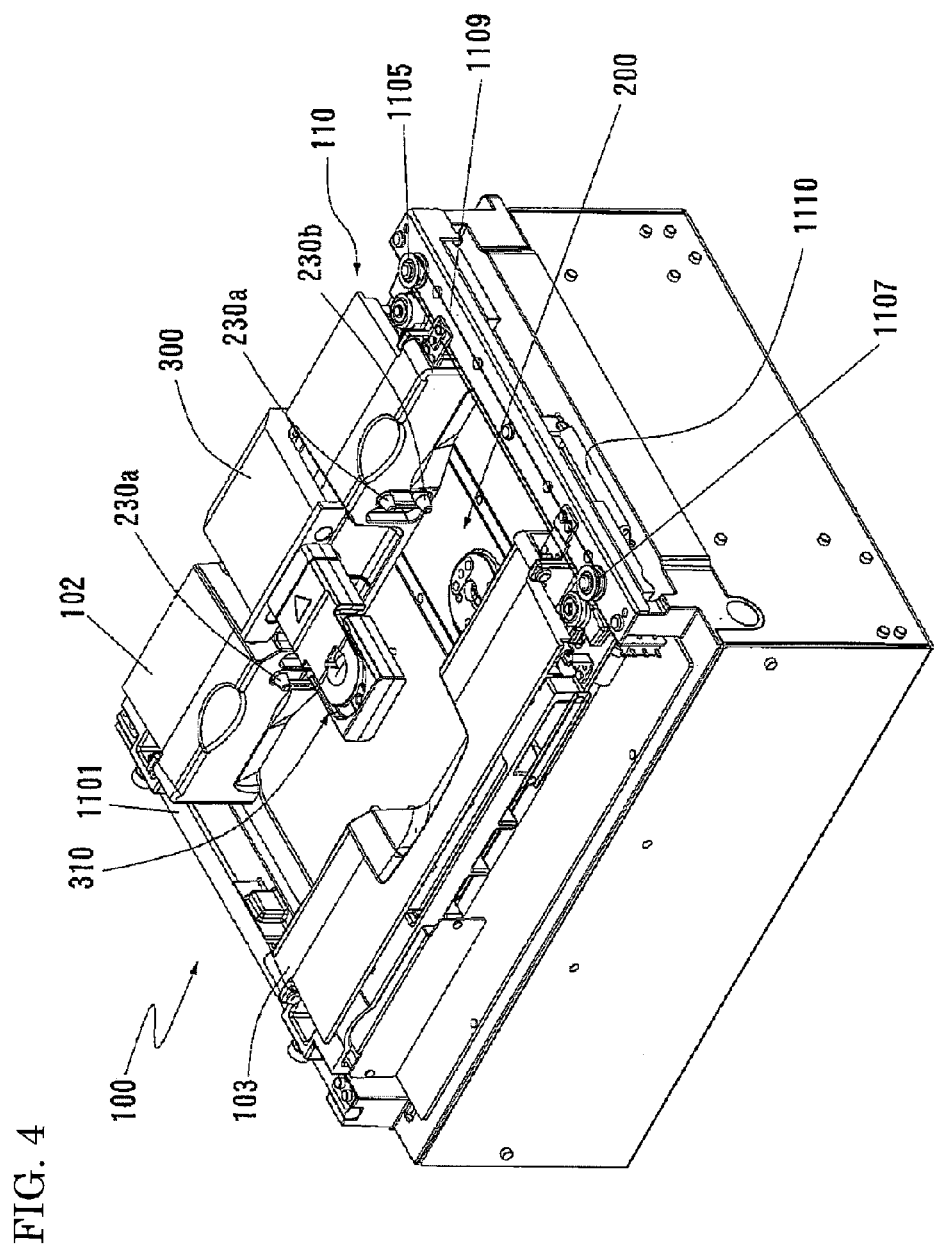
FIG. 4 is a perspective view of the frame holding unit during template measurement.
Figure 5:
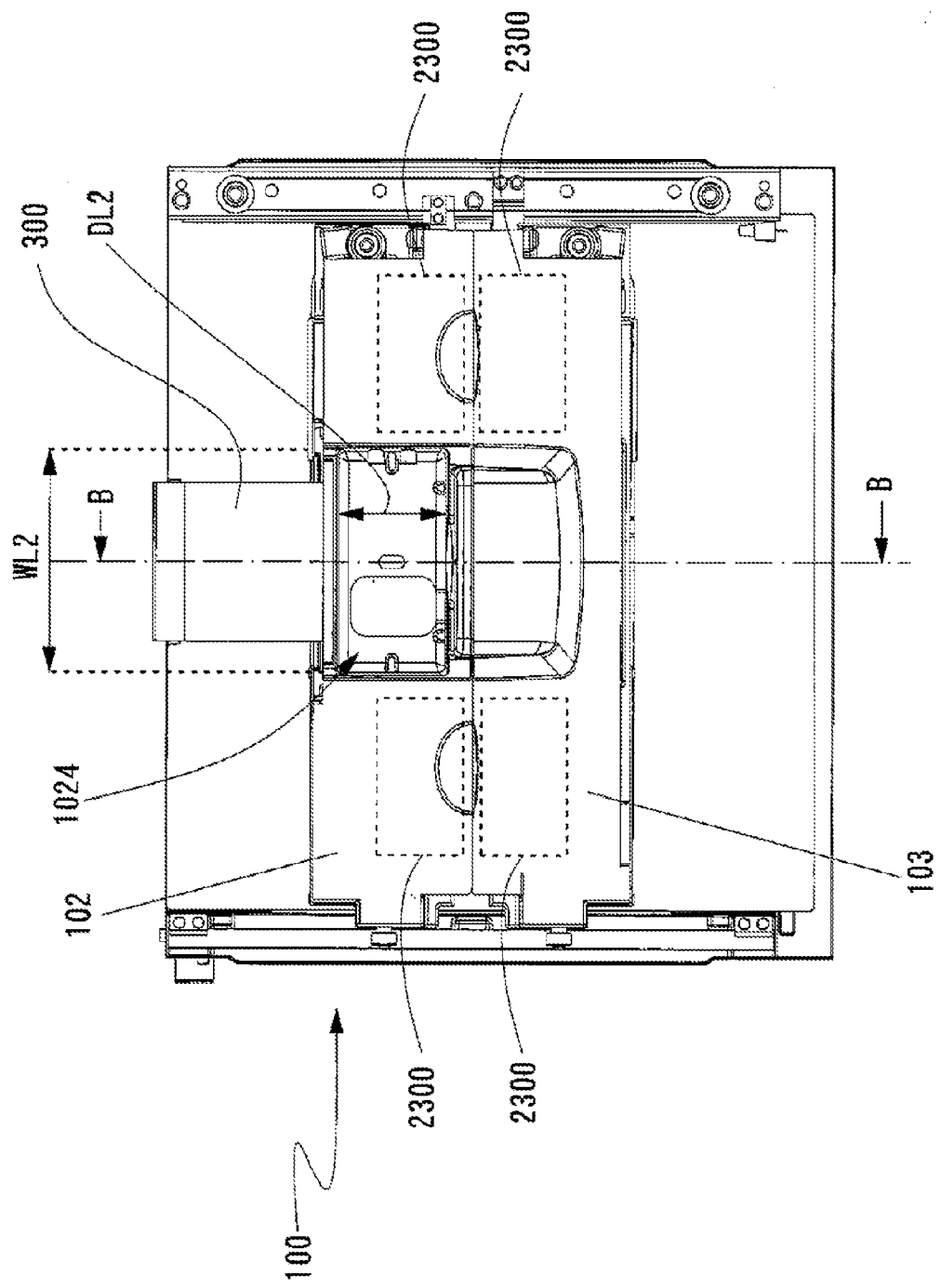
FIG. 5 is a top view of the frame holding unit in a state where a frame F is not held.

FIG. 4 is a perspective view of the frame holding unit 100 during template measurement, with the template holder 310 being attached to the attachment portion 300. FIG. 5 is a top view of the frame holding unit 100 in a state where the frame F is not held by the first slider 102 and the second slider 103.

Clamp pins 230a and 230b for clamping the top sides of the left rim RIL and the right rim RIR of the eyeglass frame F (the tops and bottoms of the rims mean the tops and bottoms in the longitudinal direction during wearing of the eyeglasses) from the thickness direction are arranged in two places, respectively, in the first slider 102. Similarly, clamp pins 230a and 230b for clamping the bottom sides of the left rim RIL and the right rim RIR in the thickness direction are also arranged in two places, respectively, in the second slider 103. The clamp pins 230a and 230b arranged in two places on the first slider 102 are arranged to protrude from the first surface 1021 to the second slider 103 side, respectively. The clamp pins 230a and 230b arranged in two places on the second slider 103 side are also arranged to protrude from the second surface 1031 to the first slider 102 side.

Figure 6:
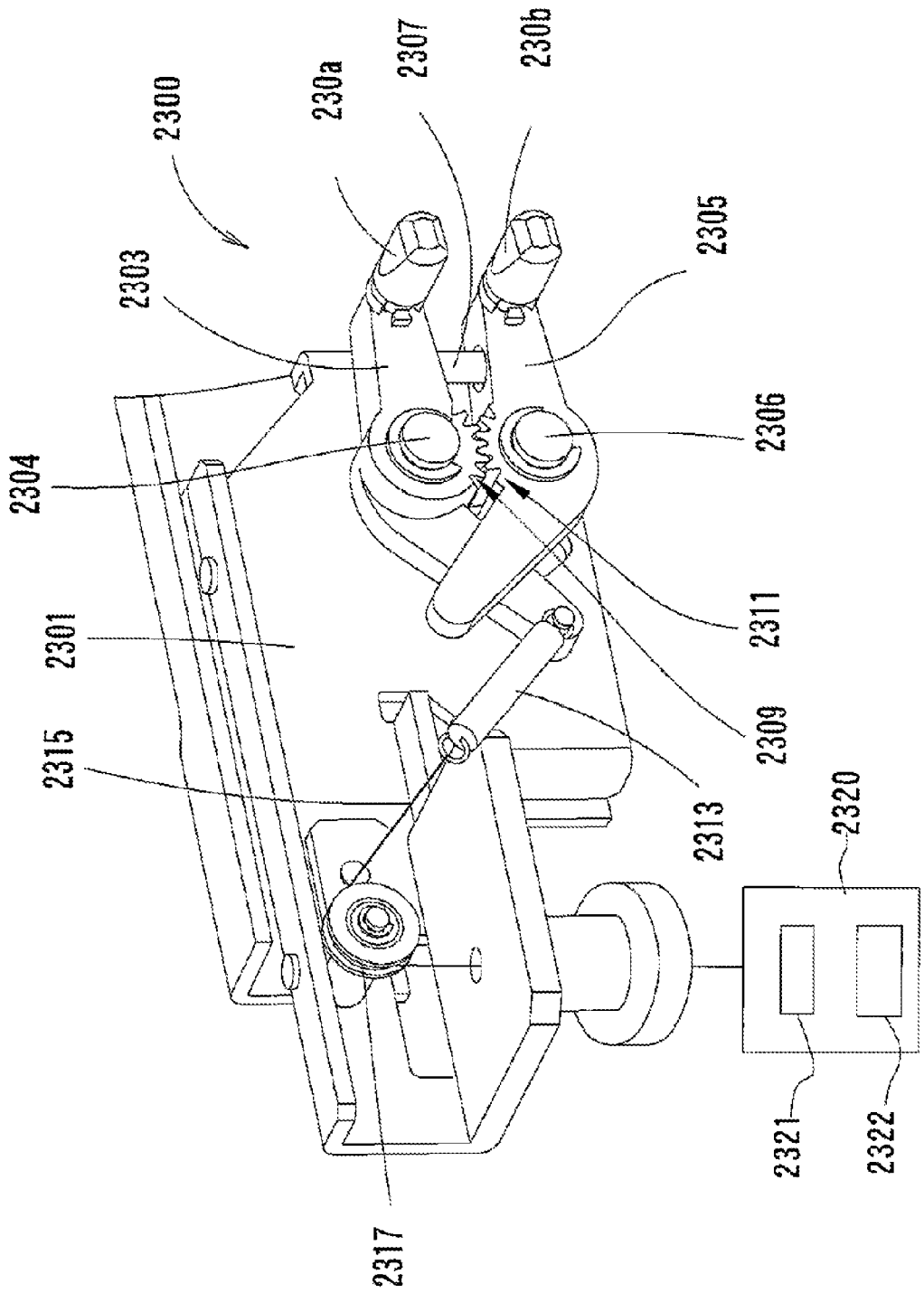
FIG. 6 is a configuration view of a clamp mechanism.

FIG. 6 is a block diagram of a clamp mechanisms 2300 arranged on the left of the first slider 102 in order to clamp the top side of the left rim RIL. A base plate 2301 is arranged inside the first slider 102. The clamp pin 230a is attached to the tip of the first arm 2303. A central portion of the first arm 2303 is held by a rotating shaft 2304 so as to be rotatable with respect to the base plate 2301. The clamp pin 230b is attached to the tip of the second arm 2305. A central portion of the second arm 2305 is held by a rotating shaft 2306 so as to be rotatable with respect to the base plate 2301. A compression spring 2307 is attached between the first arm 2303 and second arm 2305. The two clamp pins 230a and 230b are always biased by the compression spring 2307 in a direction in which the interval between the clamp pins are opened. Additionally, a gear 2309 centered on the rotating shaft 2304 is formed at the central portion of the first arm 2303. Similarly, a gear 2311 centered on the rotating shaft 2306 is formed at the central portion of the second arm 2305, and the gear 2309 meshes with the gear 2311.

One end of a spring 2313 is attached to a rear end of the first arm 2303. A wire 2315 is fixed to the other end of the spring 2313. The wire 2315 is connected to a driving unit 2320 via a pulley 2317 rotatably attached to the base plate 2301. The driving unit 2320 has a shaft 2321 for taking up a wire 2315, and a motor 2322 for rotating the shaft 2321. If the wire 2315 is pulled by the driving of the motor 2322, the first arm 2303 is rotated counterclockwise about the rotating shaft 2304. At this time, the second arm is rotated clockwise about the rotating shaft 2306 as the gear 2309 and the gear 2311 mesh with each other. Thereby, two clamp pins 230a and 230b are closed in an interlocking manner, and the rim RIL is clamped by the two clamp pins 230a and 230b.

In order to clamp the top side of the right rim RIR, a clamp mechanism arranged on the right of the first slider 102 has a configuration in which the right and left of the clamp mechanisms 2300 are inverted. Additionally, in order to clamp the bottom sides of the left rim RIL and right rim RIR, the clamp mechanisms arranged in two places of the left and right of the first slider 102 are the same as those in which the longitudinal direction thereof is inverted with respect to the clamp mechanisms 2300 arranged in the first slider 102. Therefore, the description of the other clamp mechanisms is omitted. In addition, although a configuration in which the motor 2322 and the shaft 2321 are arranged at each of the four clamp mechanisms 2300 may be adopted, a configuration in which a motor and a shaft are used commonly for the four clamp mechanisms 2300 may be adopted. In any case, a configuration in which the four clamp pins 230a and 230b may be simultaneously opened and closed may be adopted.

Figure 7:
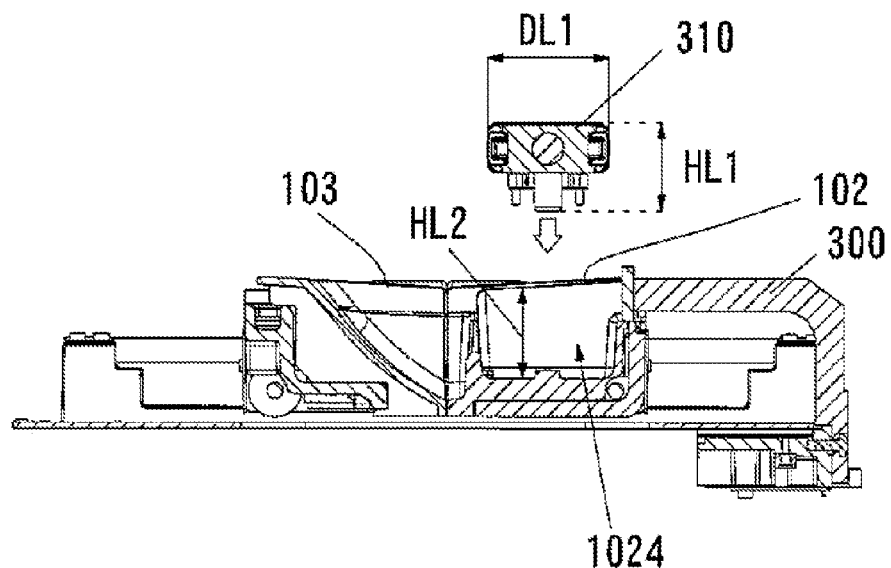
FIG. 7 is a cross-sectional view taken along line B-B in FIG. 5.

FIG. 7 is a B-B cross-sectional view of a lateral centerline LY in FIG. 5. As shown in FIGS. 3 to 5, a housing portion 1024 as a storage space (dent) for housing (storing) the template holder 310 is provided at an upper portion of the center of the first slider 102 in the lateral direction. The housing portion 1024, as shown in FIG. 5, is provided at the center between the clamp mechanisms 2300 for a left rim clamp arranged on the left of the first slider 102 and the clamp mechanisms 2300 for a right rim clamp arranged on the right of the first slider 102. As shown in FIG. 5, the lateral dimension WL2 of the housing portion 1024 in the lateral direction is formed so as to be greater than the lateral dimension WL1 of the template holder 310. The longitudinal dimension DL2 of the housing portion 1024 is formed so as to be greater than the longitudinal dimension DL1 of the template holder 310. Additionally, the height dimension HL2 of the housing portion 1024 in the perpendicular direction is formed so as to be greater than the height dimension HL1 of the template holder 310. In other words, in the configuration of the first slider 102, the lateral dimension WL1, longitudinal dimension DL1, and height dimension H11 of the template holder 310 are set so as to fall within the lateral dimension WL2, longitudinal dimension DL2, and height dimension HL2 of the housing portion 1024 that can be ensured between the clamp mechanisms 2300 for a left rim clamp and the clamp mechanisms 2300 for a right rim clamp. In addition, the housing portion 1024 may be provided between the clamp mechanisms 2300 for a left rim clamp and the clamp mechanisms 2300 for a right rim clamp on the second slider 103 side.

By providing the first slider 102 (or the second slider 103) with the housing portion 1024 in this way, it is not necessary to provide a housing place for the template holder 310 in the housing (or the housing of the eyeglass lens rim processing device in which the measurement device 1 is integrally provided) of the measurement device 1. Additionally, when the template holder 310 is used, an operator can determine the place where the template holder 310 is present visually and immediately, can take out the template holder 310 easily, and can provide the user-friendly measurement device 1 of the template holder 310.

Figure 8:
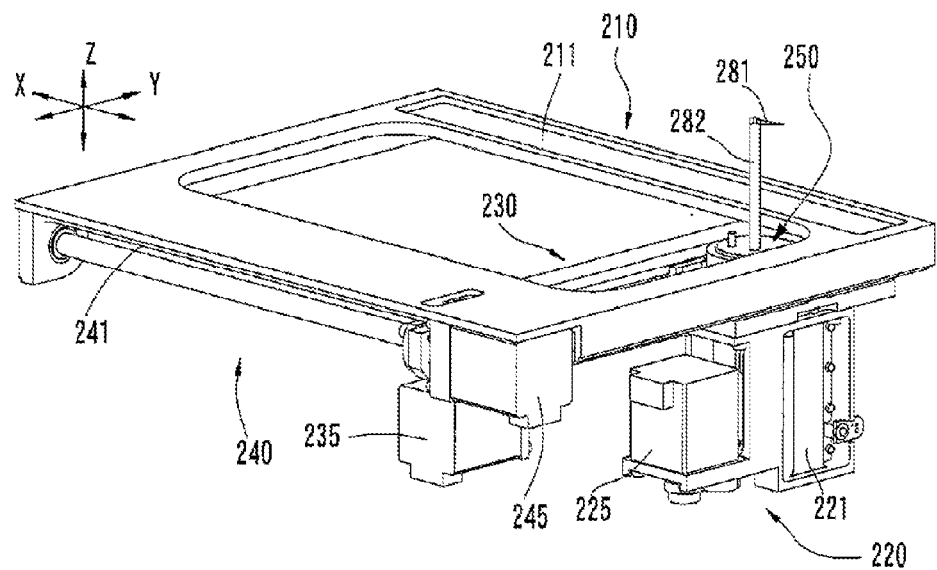
FIG. 8 is a schematic configuration view of a moving mechanism of a measuring unit.

Next, the configuration of the measuring unit 200 will be described. FIG. 8 is a schematic configuration view of an XYZ direction moving mechanism that the measuring unit 200 has. The measuring unit 200 includes a base portion 211 having a square frame that extends in the horizontal direction (XY direction), a tracing stylus holding unit 250 that holds a tracing stylus shaft 282 that has a tracing stylus 281 inserted into a groove of the rim RIL or RIR attached to the upper end thereof, and a moving unit 210 that moves the tracing stylus holding unit 250 in the XYZ directions. The base portion 211 is arranged under the frame holding unit 100. The moving unit 210 has a Y moving unit 230 that moves the tracing stylus holding unit 250 in the Y direction, an X moving unit 240 that moves the Y moving unit 230 in the X direction, and a Z moving unit 220 that moves the tracing stylus holding unit 250 in the Z direction. The Y moving unit 230 includes guide rails that extend in the Y direction, and moves the tracing stylus holding unit 250 in the Y direction along the guide rails by the driving of the motor 235. The X moving unit 240 includes guide rails 241 that extend in the X direction, and moves the Y moving unit 230 in the X direction by the driving of the motor 245. The Z moving unit 220 is attached to the Y moving unit 230, and moves the tracing stylus holding unit 250 in the Z direction by the driving of the motor 225 along the guide rails 221 that extend in the Z direction.

The configuration of the tracing stylus holding unit 250 will be described with reference to FIGS. 9, 10, 11A and 11B. The tracing stylus holding unit 250 includes a perpendicular tilt holding unit (henceforth, VH unit) 280 that holds the tracing stylus shaft 282, which has the tracing stylus 281 attached to the upper end thereof, so as to be movable in the perpendicular direction (Z direction) and that holds the tracing stylus shaft 282 so as to be tiltable in the tip direction of the tracing stylus 281 (hereinafter referred to as direction H) around a supporting point set below the tracing stylus shaft 282, and a rotating unit 260 that rotates the VH unit 280 about an axis L0 that extends in the Z direction. The tracing stylus 281 has a needlelike tip shape. Thereby, the tracing stylus 281 is easily inserted into the groove of the rim even in a case where the tracing stylus is tilted.

Figure 9:
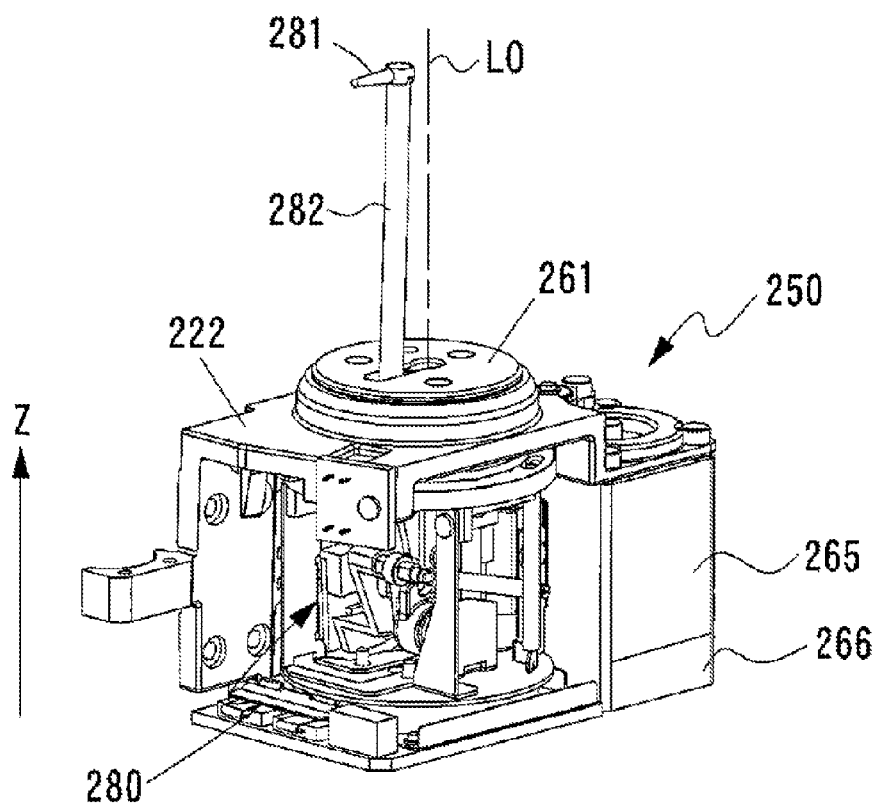
FIG. 9 is an overall perspective view of a tracing stylus holding unit.

FIG. 9 is an overall perspective view of the tracing stylus holding unit 250. The rotating unit 260 includes a rotation base 261 that holds the VH unit 280, and a motor 265 that rotates the rotation base 261. The rotation base 261 that holds the VH unit 280 is held by a Z-direction movement supporting base 222 so as to be rotatable about the axis L0. The Z-direction movement supporting base 222 is guided by the guide rails 221 shown in FIG. 8, and is moved in the Z direction by the driving of the motor 225. The rotation base 261 is rotated about the axis L0 via rotation transmission mechanisms, such as a gear, by the driving of the motor 265. The rotation angle of the rotation base 261 is detected by an encoder 266 attached to a rotating shaft of the motor 265.

Figure 10:
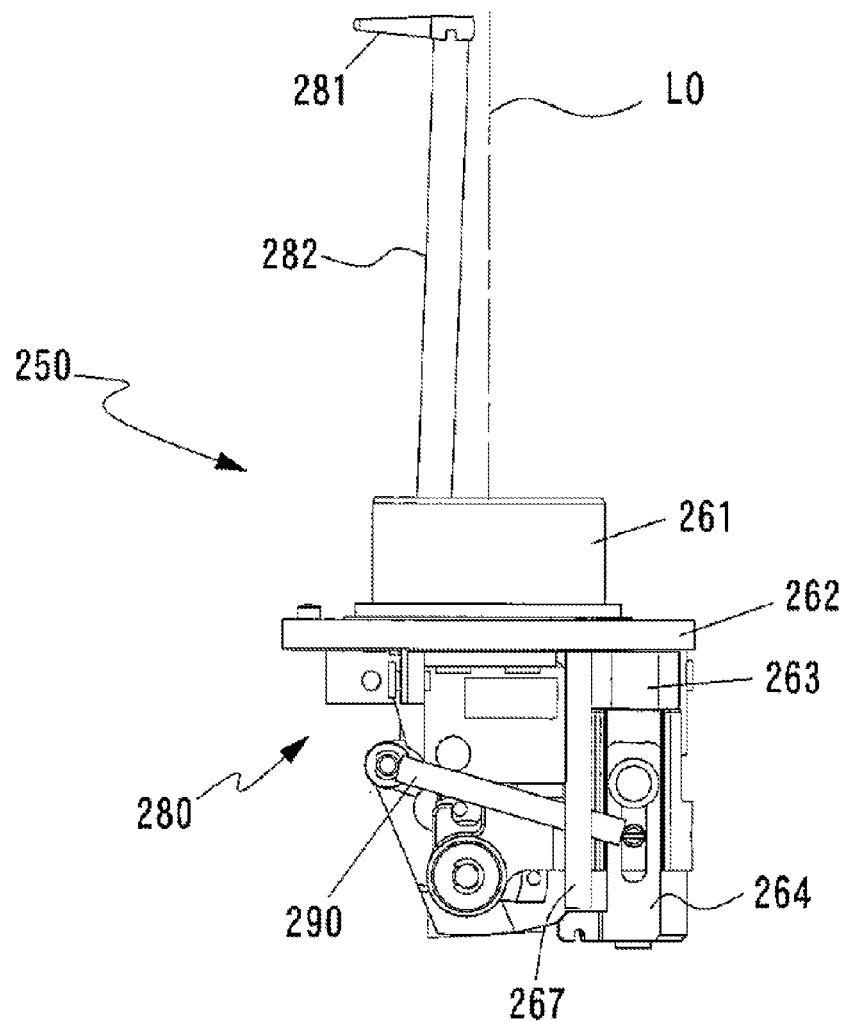
FIG. 10 is an explanatory view of a perpendicular tilt holding unit.
Figure 11A:
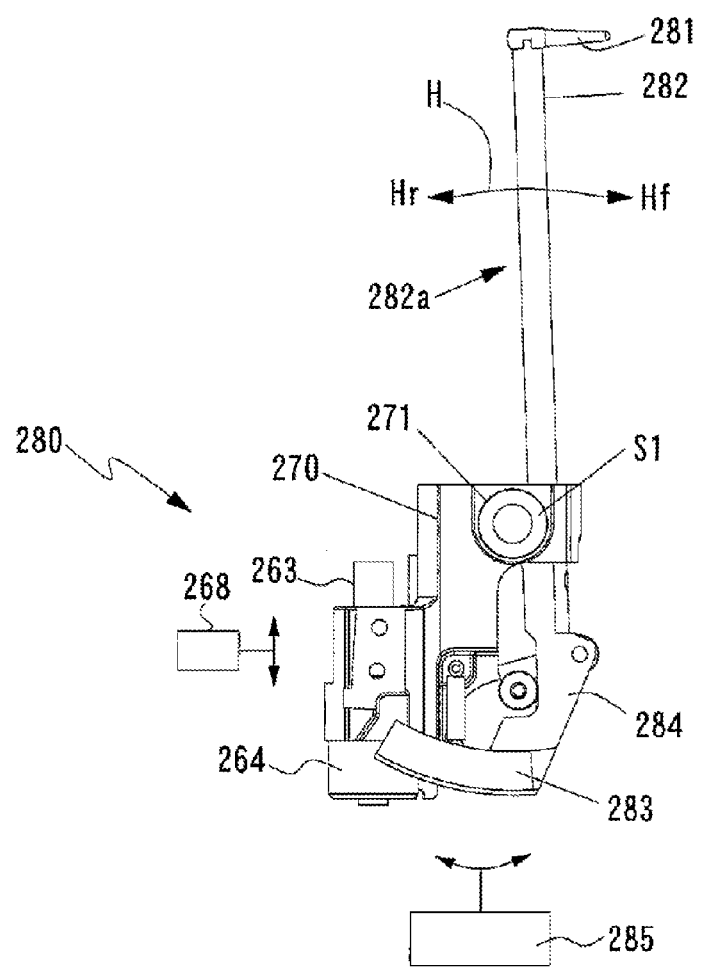
FIG. 11A is an explanatory view of the perpendicular tilt holding unit.
Figure 11B:
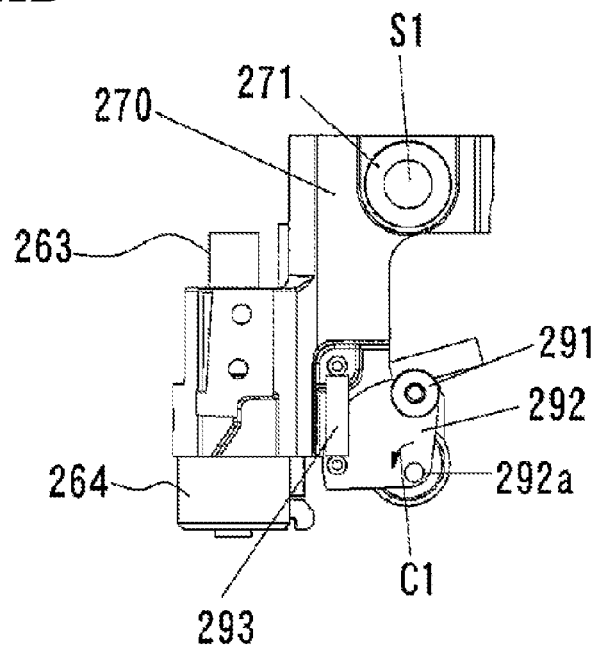
FIG. 11B is an explanatory view of the perpendicular tilt holding unit.

FIGS. 10, 11A, and 11B are explanatory views of the configuration of the VH unit 280. A guide shaft 263 that extends in the Z direction is fixed to the lower surface of a flange 262 formed integrally with the rotation base 261. The Z-direction movement supporting base 270 of the VH unit 280 is fixed to a tubular member 264 through which the guide shaft 263 passes. The VH unit 280 is held so as to be movable in the Z direction along the guide shaft 263 via the Z-direction movement supporting base 270 and the tubular member 264. Additionally, in order to mitigate the load of the VH unit 280 and/or achieve the equilibrium of the load, a spring (biasing member) 267 is attached between the flange 262 and the tubular member 264. The movement position of the VH unit 280 in the Z direction (movement position of the VH unit in the Z direction with respect to the rotation base 261) is detected by an encoder 268 that is a position detector (refer to FIG. 11A).

FIG. 11B is an explanatory view of the VH unit 280 in a state where the rotation base 261, the flange 262, and the like are removed, and is an explanatory view of the VH unit 280 seen from the back side of the drawing, with respect to FIG. 10. FIG. 11B is an explanatory view of the VH unit 280 in a state where the tracing stylus shaft 282 and the like are removed with respect to FIG. 11A. The tracing stylus shaft 282 is held so as to be tiltable in the H direction about an axis S1 (supporting point) via a bearing 271 held at an upper portion of Z-direction movement supporting base 270. A rotation angle detecting plate 283 is attached via an attachment member 284 below the tracing stylus shaft 282. The tilt angle (rotation angle) of the tracing stylus shaft 282 centered on the axis S1 in the H direction is detected by an encoder 285 that is a rotation angle detector via the rotation angle detecting plate 283.

Additionally, in order to restrict the tilt of the tracing stylus 281 in the tip direction, a restriction member 291 that abuts against the left end of the attachment member 284 is attached to a rotary plate 292, in FIG. 11A. Additionally, as shown in FIG. 10, a spring (biasing member) 290 as a first measurement pressure applying mechanism for applying measurement pressure in the tip direction of the tracing stylus 281 is arranged between the attachment plate 284 and the tubular member 264. A biasing force (measurement pressure) is always applied by the spring 290 so that the tracing stylus shaft 282 is tilted in the tip direction Hf of the tracing stylus 281. In an initial state during measurement of a rim, the tilt of the tracing stylus shaft 282 is restricted to the state of FIG. 11B by the attachment member 284 abutting against the restriction member 291. This initial state is a state where the tracing stylus shaft 282 is tilted by a predetermined angle (2 degrees) with respect to the Z-axis of a perpendicular axis in the direction Hf opposite to the tip direction of the tracing stylus 281. The rotary plate 292 is pivoted so as to be rotatable counterclockwise (in the direction of arrow C1) in FIG. 11B about a supporting point 292a below the Z-direction movement supporting base 270. The clockwise rotation of the rotary plate 292 is restricted by a restriction member (not shown). Then, a biasing force (measurement pressure during template measurement) is applied by a spring (biasing member) 293 as a second measurement pressure applying mechanism arranged between the Z-direction movement supporting base 270 and the rotary plate 292 so that the rotary plate 292 always rotates in the clockwise direction in FIG. 11B. The biasing force of the spring 293 is made greater than the biasing force of the spring 290. Thereby, the tracing stylus shaft 282 maintains the state of FIG. 11A in the initial state at the time of the measurement of the rim and the template TP. However, during the measurement of the template TP, a back surface 282a (surface located in an Hr direction opposite to the tip direction of the tracing stylus 281) of the tracing stylus shaft 282 contacts the edge of the template TP, and the tracing stylus shaft 282 is tilted in the Hf direction with the axis S1 as a supporting point as the VH unit 280 is moved in the Hr direction by the moving unit 210 controlled by the control section 50. Due to the tilt of the tracing stylus shaft 282 in the Hf direction, the attachment member 284 located below the tracing stylus shaft 282 pushes in the restriction member 291, and the rotary plate 292 is rotated in the direction of arrow C1. At this time, the measurement pressure in the Hr direction is applied to the back surface 282a of the tracing stylus shaft 282 by the spring 293. Switching is made from the first measurement pressure applying mechanism to the second measurement pressure applying mechanism during template measurement with such a configuration.

In addition, the tracing stylus shaft 282 (back surface 282a) is also used as a tracing stylus shaft that contacts the edge of the template TP. For this reason, the tracing stylus shaft 282 is adapted to be tiltable by a further 2 to 5 degrees in the Hf direction with respect to the perpendicular direction (Z direction).

Figure 12:
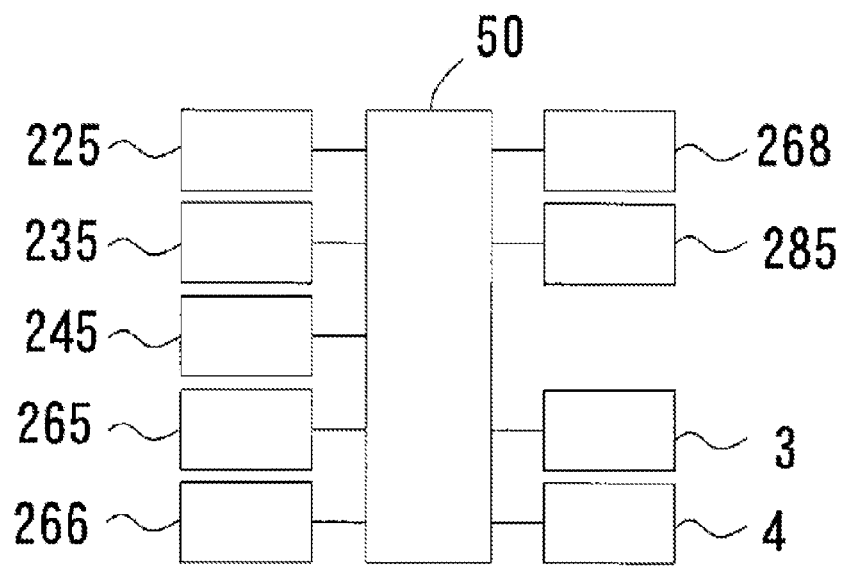
FIG. 12 is a control block diagram of the device.

FIG. 12 is a control block diagram of the device 1. The control section 50 is connected to the motors 225, 235, 245, and 265, the encoder 268 and 285, the panel section 3, and the switch section 4.

Next, the operation of the device 1 having the above configuration will be described. First, the measurement operation of a rim of the frame F will be described. The rim measurement mode and the template measurement mode can be selected by a measurement mode selection switch (measurement mode selection means) arranged in the switch section 4. Additionally, as shown in FIG. 4, if the template holder 310 is attached to the attachment portion 300 as shown in FIG. 4 in a state where the first slider 102 and the second slider 103 are opened, the first slider 102 contacts the template holder 310, and movement of the first slider 102 to the near side (operator side) is restricted. As this state is detected by a detector (not shown), a measurement mode is automatically selected as the template measurement mode, and when the first slider 102 and the second slider 103 are closed more than the state of FIG. 4, the rim measurement mode may be automatically selected.

In the rim measurement mode, during measurement of the rim RIR in the radial direction, the control section 50 determines an XY position to which the tracing stylus holding unit 250 is moved, on the basis of the measured radius vector information of the rim, and controls driving of each motor of the moving unit 210 according to the determined XY position. Preferably, the control section 50 predicts the radius vector change of a non-measured portion of the rim on the basis of the measured radius vector information of the rim, and determines the XY position to which the tracing stylus holding unit 250 is moved so that the tip of the tracing stylus 281 moves along the radius vector change of the non-measured portion.

On the basis of a measurement start signal input by the switch section 4, the control section 50 moves the tracing stylus holding unit 250 located at an initial position in the XYZ direction, and inserts the tip of the tracing stylus 281 into a groove at a measurement starting position of the rim RIR held by the clamp pins 230a and 230b (position where the rim is clamped by the clamp pins 230a and 230b of the second slider 103). The insertion of the tip of the tracing stylus 281 into the groove of the rim RIR is detected as the encoder 285 detects that the tracing stylus shaft 282 is tilted by 5 degrees in the Hr direction.

At the time of the start of measurement, the control section 50 determines that the radius vector of the rim RIR is changing in the X direction, and moves the tracing stylus holding unit 250 in the X direction. The tracing stylus shaft 282 is tilted so that the tip of the tracing stylus 281 moves to follow the radius vector change of the rim. As the tilt angle of the tracing stylus shaft 282 is detected by the encoder 285, the XY position information of the tip of the tracing stylus 281 with respect to the reference position of the tracing stylus holding unit 250 is obtained. The radius vector information of the rim is obtained by this XY position information, and the driving information of the motors 235 and 245 that perform XY movement of the tracing stylus holding unit 250.

If the radius vector information of a predetermined number of measurement points (for example, five points when 1000 points are measured as a whole) from the start of measurement is obtained, the control section 50 predicts the changes of the next measurement points (non-measured points) on the basis of the measured radius vector information, and moves the tracing stylus holding unit 250 in the XY direction on the basis of the result so that the tracing stylus 281 runs along the rim RIR. Additionally, the control section 50 controls the driving of the motor 265 and rotates the rotation base 261 to thereby rotate the VH unit 280 about the axis L0. The rotation angle at this time is determined so that the tip direction of the tracing stylus 281 becomes a direction that is normal to the predicted radius vector change of the rim. Otherwise, the rotation angle is determined as a radial angle centered on a reference point at the time of the start of measurement of the rim (a point on the centerline LX in FIG. 3 in the Y direction of a measurement start point). Otherwise, the rotation angle is determined as the angle between the radial angle centered on the reference point at the time of the start of measurement and the direction that is normal to the radius vector change of the rim. The radius vector information of the whole circumference of the rim is measured by repeating this operation.

Additionally, as for the position of the rim in the Z direction from the start of measurement, the tracing stylus shaft 282 is moved in the Z direction along with the tracing stylus 281 so as to follow the change of the rim in the Z direction. As the movement position of the tracing stylus shaft 282 in the Z direction is detected by the encoder 268, the Z position information of the tracing stylus shaft 282 with respect to the reference position of the tracing stylus holding unit 250 is obtained. The Z position information of the rim is obtained by this Z position information, and the driving information of the motor 225 that performs Z movement of the tracing stylus holding unit 250.

If the Z position information of a predetermined number of measurement points (five points) from the start of measurement is obtained, the control section 50 predicts the changes in the positions of the next measurement points (non-measured points) on the basis of the measured Z position information, and moves the tracing stylus holding unit 250 in the Z direction on the basis of the result so that the tracing stylus 281 runs along the rim. Additionally, in a case where the rim is curved upward from the measurement starting point (in a case where the Z position of the non-measured point increases upward), the control section 50 performs XY movement of the tracing stylus holding unit 250 so that the tracing stylus shaft 282 is greatly tilted in the Hr direction according to the height of the Z position. Thereby, the direction of the tip of the tracing stylus 281 is tilted according to the tilt of the rim RIR. For this reason, even when a rim with a high curved frame is measured, the tracing stylus 281 is not easily separated from the rim, and a high curve frame can be measured with high precision. The Z position information of the whole rim is measured by repeating this operation.

Next, the measurement operation of the template TP will be described. After an operator attaches the template holder 310 to the attachment portion 300 in a predetermined state, the operator selects the template measurement mode using the switch of the switch section 4 (or the template measurement mode is automatically selected), and pushes a measurement start switch to start measurement of the template TP. The control section 50 moves the tracing stylus holding unit 250 located at the initial position in the XY direction so that the edge position of the template TP on the centerline LX (refer to FIG. 3) becomes the measurement start point. Additionally, in the measurement start point, the control section 50 controls the driving of the motor 265 of the rotating unit 260 and rotates the tracing stylus holding unit 250 so that the back surface 282a of the tracing stylus shaft 282 located in the direction (Hr direction) opposite the tip of the tracing stylus 281 faces the edge of the template TP.

In addition, the VH unit 280 is located at the lowest point with respect to the tracing stylus holding unit 250 in the initial state, and the Z position of the VH unit 280 is set so that the distance between the central height of the template TP held by the template holder 231 and the axis S1 that is the tilt center of the tracing stylus shaft 282 becomes a predetermined distance (40 mm).

When the back surface 282a of the tracing stylus shaft 282 contacts the edge of the template TP and the tracing stylus holding unit 250 is further moved to the template TP side by the movement of the tracing stylus holding unit 250 to the template TP side, the tracing stylus shaft 282 is tilted in the Hf direction against the biasing force of the spring 293. The tilt angle of the tracing stylus shaft 282 in the Hf direction is detected by the encoder 285. If the tracing stylus shaft 282 takes a perpendicular direction (coincides with the Z direction), the control section 50 stops the movement of the tracing stylus holding unit 250 to the template TP side and starts measurement from this time point.

During the measurement of the template TP, the control section 50 determines the XY position of the tracing stylus holding unit 250 and the rotation angle of the rotating unit 260 and controls the driving of the moving unit 210 and the rotating unit 260 so that the tracing stylus shaft 282 is located in the perpendicular direction, on the basis of the measured radius vector information of the template TP. Preferably, the control section 50 predicts the radius vector change of a non-measured portion of the template TP on the basis of the measured radius vector information of the template TP, and determines the XY position of the tracing stylus holding unit 250 and the rotation angle of the rotating unit 260 so that the tracing stylus shaft 282 moves along the radius vector change of the non-measured portion while kept perpendicular.

At the time of the start of measurement, the control section 50 determines that the radius vector of the template TP is changing in the Y direction, and moves the tracing stylus holding unit 250 in the Y direction. If the actual radius vector of the template TP is changing with respect to a scheduled direction (the Y direction at the time of the start of measurement) of the radius vector of the template TP, the tracing stylus shaft 282 is tilted in the H direction (Hr or Hf direction) so as to follow the change, and deviate with respect to the perpendicular direction. The tilt angle of the tracing stylus shaft 282 with respect to the perpendicular direction is detected by the encoder 285. In a case where the tracing stylus shaft 282 is kept perpendicular, the radius vector information of the template TP is obtained as the XY position information of the tracing stylus holding unit 250. In a case where the tracing stylus shaft 282 is tilted with respect to the perpendicular direction, however, correction is made by the corresponding amount.

If the tilt angle of the tracing stylus shaft 282 with respect to the perpendicular direction is α and the distance from the height center of the template to the tilt center (axis S1) of the tracing stylus shaft 282 is L, the radius correction amount ΔR of the radius vector is obtained by $$\Delta R = L \times \sin \alpha.$$

This operation is performed by the control section 50. The control section 50 obtains the radius vector information of the template TP on the basis of this correction operation and the driving information of the motors 235 and 245 that perform the XY movement of the tracing stylus holding unit 250.

In addition, although the point where the template TP contacts the back surface 282a of the tracing stylus shaft 282 deviates slightly according to a difference in the thickness of the template TP (a difference in the height position of the edge in the case of the demo lens), this is within an allowable error in template measurement, and practical precision is ensured.

If the radius vector information of a predetermined number of measurement points (five points) from the start of measurement is obtained, the control section 50 predicts the changes of the next measurement points (non-measured points) on the basis of the measured radius vector information, and moves the tracing stylus holding unit 250 in the XY direction on the basis of the result so that the tracing stylus shaft 282 runs along the edge of the template TP while being kept perpendicular. Additionally, the control section 50 controls the driving of the motor 265 and rotates the rotation base 261 to thereby rotate the VH unit 280. The rotation angle at this time is determined so that the back surface 282a of the tracing stylus shaft 282 becomes the direction that is normal to the radius vector of the template TP. Otherwise, the rotation angle is determined as a radial angle based on the holding center of the template holder 310. Otherwise, the rotation angle is determined as the angle between the radial angle based on the holding center of the template holder 310 and the direction that is normal to the radius vector change of the rim. The radius vector information of the whole rim is measured by repeating this operation. The radius vector information of the whole circumference of the template TP is measured by repeating this operation.

In addition, in a case where the tilt angle of the tracing stylus shaft 282 detected by the encoder 285 deviates from a prescribed range (for example, 0.5 degrees) with respect to the perpendicular direction during template measurement, the control section 50 determines the shape of the rim as an untraceable shape, stops the template measurement, and issues a warning message using an alarm (display 3). The untraceable shape has irregularities with a diameter smaller than the radius of the tracing stylus shaft 282.

As described above, even in the configuration in which the tracing stylus shaft 282 is tilted according to the height of a rim in order to measure the rim RIR (RIL) with a high curve frame with high precision, the back surface 282a (surface opposite the tip direction of the tracing stylus 281) of the tracing stylus shaft 282 can be used as a measurement surface that contacts the edge of the template TP. Through this configuration, a moving mechanism and a detecting mechanism for measurement of a rim can be shared, and the precision of template tracing can be improved. Additionally, since it is not necessary to provide a tracing stylus shaft exclusively for template tracing, a complicated configuration and high costs can be avoided.

What is claimed is:

1. An eyeglass frame shape measurement device comprising:
   an eyeglass frame holding unit including a first slider and a second slider which are configured to hold an eyeglass frame;
   a rim measuring unit including a tracing stylus to be inserted into a groove of a rim of the eyeglass frame, the rim measuring unit being configured to detect the movement position of the tracing stylus to measure a shape of the rim;
   a template holder configured to attach one of a measurement object of a demo lens and a template;
   a template measuring unit including a tracing stylus shaft configured to contact an edge of the measurement object attached to the template holder, the template measuring unit being configured to detect the movement of the tracing stylus shaft in a radial direction of the measurement object to measure radius vector information of the measurement object; and
   a housing portion provided to house the template holder and provided in one of the first slider and the second slider when measurement using the template measuring unit is not being performed.

2. The eyeglass frame shape measurement device according to claim 1, wherein
   each of the first slider and the second slider includes a left rim clamp mechanism including a clamp pin for clamping a left rim and a right rim clamp mechanism including a clamp pin for clamping a right rim,
   at least one of the first slider and the second slider has a space formed between the left rim clamp mechanism and the right rim clamp mechanism,
   the space being formed by denting an upper portion of the slider, and
   the housing portion is provided in the space.

3. The eyeglass frame shape measurement device according to claim 1, wherein
   an upper portion of a center of one of the first slider and the second slider in a lateral direction in which the first slider and the second slider extend is dented, and the housing portion is provided in the space.

4. The eyeglass frame shape measurement device according to claim 1 further comprising an attachment portion to which the template holder is detachably attached.

5. The eyeglass frame shape measurement device according to claim 1, wherein the template holder has a lateral dimension, a longitudinal dimension, and a height dimension so as to fall within a lateral dimension, a longitudinal dimension, and a height dimension of the housing portion.

6. The eyeglass frame shape measurement device according to claim 1, wherein
   the rim measuring unit includes:
   a tracing stylus holding unit including a tracing stylus shaft that has the tracing stylus attached to an upper portion thereof, the tracing stylus holder unit being configured to hold the tracing stylus shaft so as to be tiltable in a tip direction of the tracing stylus;
   a tilt angle detecting unit configured to detect a tilt angle of the tracing stylus shaft;
   a moving unit configured to two-dimensionally move the tracing stylus holding unit in the radial direction of the rim; and
   a rotating unit configured to rotate the tracing stylus holding unit around an axis perpendicular to the radial direction, and the rim measuring unit is used as the template measuring unit, and the tracing stylus shaft is used as the tracing stylus shaft that contacts the edge of the measurement object, the eyeglass frame shape measurement device further comprises:

a measurement mode selection unit configured to select a rim measurement mode and a template measurement mode;

a control unit configured to control the rotating unit and the moving unit so that a back surface of the tracing stylus shaft located opposite the tracing stylus shaft contacts the edge of the measurement object in template measurement mode; and an arithmetic unit configured to obtain the radius vector information of the measurement object based on position information of the tracing stylus holding unit in the radial direction, rotation information of the rotating unit, and detection information of the tilt angle detecting unit, and during measuring the measurement object, the control unit controls the rotating unit and the moving unit so that the tilt of the tracing stylus shaft is kept perpendicular to the edge of the measurement object when the back surface of the tracing stylus shaft contacts the edge of the measurement object, based on the detected information.

7. The eyeglass frame shape measurement device according to claim 6, wherein the arithmetic unit corrects the position information of the tracing stylus holding unit in the radial direction to obtain the radius vector information of the measurement object, based on the tilt angle detected by the tilt angle detecting unit.

8. The eyeglass frame shape measurement device according to claim 6 further comprising:

a first measurement pressure applying mechanism configured to apply measurement pressure so that the tracing stylus shaft is tilted in the tip direction of the tracing stylus in the rim measurement mode;

a second measurement pressure applying mechanism configured to apply measurement pressure so that the back surface of the tracing stylus shaft is tilted toward the edge of the measurement object in the template measurement mode; and a switching unit configured to switch between the first measurement pressure applying mechanism and the second measurement pressure applying mechanism.

9. The eyeglass frame shape measurement device according to claim 6, wherein the control unit stops the measurement operation of the template measuring unit in a case where the tilt angle detected by the tilt angle detecting unit exceeds a predetermined range.

* * * * *